(12) United States Patent
Alper

(10) Patent No.: US 8,828,731 B2
(45) Date of Patent: *Sep. 9, 2014

(54) METHOD AND SYSTEM FOR ANALYZING CONCENTRATIONS OF DIVERSE MERCURY SPECIES PRESENT IN A FLUID MEDIUM

(75) Inventor: Hal Alper, Flowery Branch, GA (US)

(73) Assignee: MyCelx Technologies Corporation, Duluth, GA (US)

( * ) Notice: Subject to any disclaimer, the term of this patent is extended or adjusted under 35 U.S.C. 154(b) by 57 days.

This patent is subject to a terminal disclaimer.

(21) Appl. No.: 13/392,357

(22) PCT Filed: Aug. 27, 2010

(86) PCT No.: PCT/US2010/002356
§ 371 (c)(1),
(2), (4) Date: Apr. 6, 2012

(87) PCT Pub. No.: WO2011/046581
PCT Pub. Date: Apr. 21, 2011

(65) Prior Publication Data
US 2012/0184039 A1 Jul. 19, 2012

Related U.S. Application Data

(63) Continuation-in-part of application No. 12/459,389, filed on Jun. 30, 2009, now Pat. No. 8,105,423, which is a continuation-in-part of application No. 12/001,057, filed on Dec. 7, 2007, now Pat. No. 7,981,298.

(60) Provisional application No. 60/874,915, filed on Dec. 14, 2006, provisional application No. 61/275,349, filed on Aug. 28, 2009.

(51) Int. Cl.
*B01D 15/08* (2006.01)
*B01D 53/02* (2006.01)
*G01N 33/20* (2006.01)
*G01N 1/40* (2006.01)
*G01N 21/73* (2006.01)
*B01D 53/04* (2006.01)
*G01N 1/20* (2006.01)
*G01N 21/31* (2006.01)

(52) U.S. Cl.
CPC .............. *G01N 1/4077* (2013.01); *G01N 21/73* (2013.01); *B01D 53/04* (2013.01); *B01D 2257/602* (2013.01); *G01N 2001/2064* (2013.01); *B01D 53/025* (2013.01); *G01N 21/3103* (2013.01); *B01D 2253/306* (2013.01); *G01N 1/2035* (2013.01); *B01D 2253/102* (2013.01)
USPC ................. 436/81; 436/76; 210/662; 95/134; 423/210

(58) Field of Classification Search
CPC ... G01N 33/20; G01N 33/0045; G01N 31/22; G01N 33/1813; G01N 21/3103; G01N 33/84; G01N 25/4873; B01D 15/08; B01D 53/0415; B01D 2253/102; B01D 2253/106; B01D 53/64; B01D 2257/602; B01D 53/02; B01D 53/04; B01D 53/34; B01D 2257/302; C02F 1/42; C02F 1/283; C02F 1/281; C02F 2303/16; B01J 49/0095
USPC .......... 436/81, 76; 210/662; 95/134; 423/210
See application file for complete search history.

(56) References Cited

U.S. PATENT DOCUMENTS

| | | |
|---|---|---|
| 1,808,170 A | 6/1931 | Kamrath |
| 2,107,945 A | 2/1938 | Hull et al. |
| 3,627,191 A | 12/1971 | Hood |
| 3,786,619 A | 1/1974 | Melkersson et al. |
| 4,050,237 A | 9/1977 | Pall et al. |
| 4,154,704 A | 5/1979 | Vinton et al. |
| 4,160,684 A | 7/1979 | Berger, Jr. et al. |
| 4,233,274 A | 11/1980 | Allgulin |
| 4,416,408 A | 11/1983 | Spirig |
| 4,443,341 A | 4/1984 | Miller et al. |
| 4,705,543 A | 11/1987 | Kertzman |
| 4,925,463 A | 5/1990 | Kuhnert |
| 5,080,799 A | 1/1992 | Yan |
| 5,292,412 A | 3/1994 | Pitton |
| 5,409,522 A | 4/1995 | Durham et al. |

| | | | |
|---|---|---|---|
| 5,437,793 | A | 8/1995 | Alper |
| 5,698,139 | A | 12/1997 | Alper |
| 5,733,786 | A | 3/1998 | Green |
| 5,837,146 | A | 11/1998 | Alper |
| 5,961,823 | A | 10/1999 | Alper |
| 5,972,216 | A | 10/1999 | Acernese et al. |
| 6,117,333 | A | 9/2000 | Frankiewicz et al. |
| 6,180,010 | B1 | 1/2001 | Alper |
| 6,268,543 | B1 | 7/2001 | Sakai et al. |
| 6,475,802 | B2 | 11/2002 | Schaedlich et al. |
| 6,805,727 | B2 | 10/2004 | Alper |
| 6,811,588 | B2 | 11/2004 | Niakin |
| 6,861,002 | B2 | 3/2005 | Hughes |
| 6,958,136 | B2 | 10/2005 | Chandran et al. |
| 7,041,222 | B1 | 5/2006 | Rainer |
| 7,211,707 | B2 | 5/2007 | Axtell et al. |
| 7,264,721 | B2 | 9/2007 | Alper |
| 7,264,722 | B2 | 9/2007 | Alper |
| 7,309,429 | B2 | 12/2007 | Patil et al. |
| 7,476,365 | B2 | 1/2009 | Al-Faqeer |
| 7,708,794 | B2 | 5/2010 | Dullien et al. |
| 7,981,298 | B2 | 7/2011 | Alper |
| 8,062,517 | B2 | 11/2011 | Alper |
| 8,105,423 | B2 | 1/2012 | Alper |
| 2002/0027105 | A1 | 3/2002 | Alper |
| 2003/0228699 | A1 | 12/2003 | Shade et al. |
| 2005/0207955 | A1 | 9/2005 | Wang |
| 2006/0011551 | A1* | 1/2006 | Alper ............ 210/680 |
| 2006/0021506 | A1 | 2/2006 | Hakka et al. |
| 2007/0092418 | A1 | 4/2007 | Mauldin et al. |
| 2007/0289447 | A1 | 12/2007 | Yang et al. |
| 2008/0011683 | A1* | 1/2008 | Dong et al. ............ 210/662 |
| 2008/0081376 | A1 | 4/2008 | Hernandez et al. |
| 2008/0210635 | A1 | 9/2008 | Alper |
| 2009/0029447 | A1 | 1/2009 | Squire |
| 2009/0032472 | A1 | 2/2009 | Krogue et al. |
| 2009/0101015 | A1 | 4/2009 | Hua |
| 2009/0145343 | A1 | 6/2009 | Mauldin |
| 2010/0000409 | A1 | 1/2010 | Alper |

FOREIGN PATENT DOCUMENTS

| | | | |
|---|---|---|---|
| CH | 340483 | A | 8/1959 |
| JP | 2001-011548 | A | 1/2001 |
| WO | 2008/076314 | A2 | 6/2008 |
| WO | 2011/002493 | A1 | 1/2011 |
| WO | 2011/046581 | A1 | 4/2011 |

OTHER PUBLICATIONS

PCT International Search Report and Written Opinion dated Nov. 8, 2010 for PCT/US2010/02356.
Patent Examination Report No. 1 for Australian Patent Application No. 2010266695 issued Aug. 3, 2013.
Supplementary European Search Report mailed Nov. 19, 2012 for EP10794482.
International Preliminary Report on Patentability for International Application No. PCT/US2010/002356 issued Feb. 28, 2012.
International Search Report for International Application No. PCT/US2010/001824 mailed Aug. 23, 2010.
Written Opinion for International Application No. PCT/US2010/001824 mailed Aug. 23, 2010.
International Preliminary Report on Patentability for International Application No. PCT/US2010/001824 issued Jan. 4, 2012.
International Search Report for International Application No. PCT/US2007/025514 mailed Apr. 17, 2008.
Written Opinion for International Application No. PCT/US2007/025514 mailed Apr. 17, 2008.
International Preliminary Report on Patentability for International Application No. PCT/US2007/025514 issued Jun. 16, 2009.

* cited by examiner

*Primary Examiner* — Krishnan S Menon
*Assistant Examiner* — Dwan A Gerido
(74) *Attorney, Agent, or Firm* — Sutherland Asbill & Brennan LLP

(57) ABSTRACT

A method for facilitating removal of mercury from a primary fluid stream of interest which is contaminated with organically-bound, elemental, and ionic mercury species. The stream is analyzed to establish the relative content of the organically-bound, elemental, and ionic mercury species present therein by forming a diverted side stream from the primary stream, and passing the side stream successively through three in series filter stages, the first captures organically bound mercury, the second captures elemental mercury, and the third captures ionic mercury. The side stream flow through the filter stages is continued for a predetermined period, and upon conclusion of the period the quantity of mercury collected at each of the filtration stages is determined. This data is then utilized to determine the capacity of the three different filtration stages required to reduce the mercury content in the mam stream to a desired level.

28 Claims, 2 Drawing Sheets

METHOD AND SYSTEM FOR ANALYZING CONCENTRATIONS OF DIVERSE MERCURY SPECIES PRESENT IN A FLUID MEDIUM

CROSS REFERENCE TO RELATED APPLICATIONS

This application is a U.S. national stage application of International Application Number PCT/US2010/002356, filed Aug. 27, 2010, which claims priority to U.S. provisional patent application No. 61/275,349 filed on Aug. 28, 2009, which is incorporated herein by reference in its entirety. This application also is a continuation-in-part of U.S. Ser. No. 12/459,389, now U.S. Pat. No. 8,105,423, filed on Jun. 30, 2009, which is a continuation-in-part of U.S. Ser. No. 12/001,057 filed on Dec. 7, 2007, now U.S. Pat. No. 7,981,298, which claims priority from U.S. provisional application Ser. No. 60/874,915 filed on Dec. 14, 2006, each of which is incorporated herein by reference in their entireties.

FIELD OF INVENTION

This invention relates generally to methods and apparatus for analyzing the concentrations of diverse contaminating mercury species present in a fluid stream, in order that an effective strategy for separating the mercury from the stream may then be formulated.

BACKGROUND OF INVENTION

In the course of practicing a wide variety of commercially important industrial processes, aqueous or gaseous process streams (or more generally "fluid streams") are produced which are contaminated with pernicious quantities of mercury. Mercury is corrosive to metals and other materials within the facility where the process is practiced, and is harmful to human health and to the surrounding ecosystem. The mercury contaminants have proved to be particularly difficult to remove or reduce to acceptable levels. In order to do so, it is important to know the concentration and speciation (organically-bound, ionic, or elemental) of mercury (Hg) in the stream containing same.

An important example of the type of operation to which the present invention is directed arises in the operation of oil and gas exploration and drilling facilities maintained upon platforms in natural or other bodies of water, including so-called "off shore drilling platforms". In conducting operations at these platforms, industrial streams are developed (often referred to as "produced water") which by virtue of the processes conducted contain comparatively large quantities of mercury, present in the form of the three species mentioned above. Such a produced water stream is exemplified herein as an aqueous system to which the invention is directly applicable, but it will be understood that the invention is in no way so limited, but may be used with a large variety of other industrial streams that have become contaminated with mercury during or as a result of the industrial process, or even more generally with any aqueous system which is contaminated with mercury in the forms mentioned.

Furthermore, in the course of practicing a wide variety of commercially important industrial processes, gaseous process streams (or more generally "gaseous streams") are produced which are contaminated with pernicious quantities of mercury. Here again, the mercury contaminants have proved to be particularly difficult to remove or reduce to acceptable levels. One of the most pernicious forms of mercury pollution in such gaseous streams is finely aerosolized elemental mercury. This form of mercury is generated by coal-fired power generation and is present in natural gas. In the U.S., coal-fired power plants are the largest source of man-made mercury emissions to the air, accounting for approximately 40% of all mercury emissions. Under current circumstances, mercury is adsorbed on the aerosolized soot from coal burning. This soot eventually settles and the mercury adsorbed on the carbon is converted to methyl mercury, dimethyl mercury, and other forms, which accumulate in the food chain. Alternatively, techniques have been developed which will cause the carbonaceous soot to auto-ignite and convert to $CO_2$ and $H_2O$. When this occurs, finely aerosolized elemental mercury is produced. The mechanism for conversion of elemental mercury to methyl mercury and other forms is not well understood, but is most certainly microbially mediated. It is estimated that 2000 tons of mercury is generated this way annually. Elemental mercury also occurs in natural gas in concentrations up to hundreds of micrograms per $Nm^3$. This is a significant amount considering that a typical plant will process millions of $Nm^3$ per day.

Characterization of the Hg species is therefore critical in designing remediation technology, as the three primary forms of mercury (ionic, organically-bound, and elemental) possess very different physical and chemical properties. However, up to now, the ability to characterize mercuric species has been limited and difficult. The reasons are as follows:

1) Mercury is usually present in very low concentrations (usually 1 ppm or less) and there are usually large fluctuations in influent mercury concentration; rendering inaccurate spot sampling;

2) The composition of speciation changes when these small amounts of mercury come in contact with the sample vessel; and 3) Standard tests are destructive and do not differentiate adequately between the three forms.

SUMMARY OF INVENTION

The present invention encompasses a method and means of in-situ sampling and characterization, which overcomes the above limitations. The method of the invention is practiced in a filtration system composed of three distinct filtration stages, with each stage having a specific affinity for each of the three predominant forms of mercury. The first stage is composed of filtration devices, which visco-elastically coagulate and incorporate substantially all organically bound forms of Hg. The second stage is a filter constructed with gold-plated solder wick as the elemental Hg collection media. The finely braided wires in these filters are able to intercept and capture elemental dispersed minute particles of mercury from the fluid stream passed there through. The third stage is composed of a granular media adapted to collect the ionic mercury. In this context the term "ionic mercury" refers not only to such ions as may be present in an aqueous stream, but essentially means or is synonymous with inorganic mercury salts. Such salts may be present in the gaseous stream where they are hydrated by water vapor in the gases. In the case of a gaseous stream, the collecting media can simply comprise a granular activated carbon. In the instance of an aqueous stream, the media can comprise one impregnated with one or more chemical agents that are able to precipitate the ionic mercury. The granular media can in this latter instance be composed of carbon, clay, paper, perlite, etc., and the precipitating agents can include, but are not limited to, calcium sulfate, sulfides and thiols.

The system is supplied by a side stream (e.g. with an aqueous stream, 1 to 5 gal/min) diverted from the primary stream of interest (e.g. 100s to 1000s of gal/min of produced water), and allowed to operate for a predetermined sampling period, depending on the influent concentrations. Each one of the filtration stages accumulates the species of mercury for which it has particular affinity. By concentrating the different species over an extended period of time, this approach overcomes the difficulties caused by attempting to spot sample for low concentrations, fluctuation in influent concentration, and alteration of species after sampling. The sampling period can vary depending on the flow conditions and the concentrations of the Hg in the stream. In some aqueous streams the period can e.g. be from one day to several weeks. But it is not so much a matter of how much or how long the collection is; rather, the overriding principle is that by analyzing the influent and effluent aqueous stream we are measuring how much is being intercepted in real time and over time In the case of an aqueous stream, the stream is sampled before flowing through the first filtration stage with an aqueous grab sample. Following the predetermined flow period, filtered aqueous samples are taken after each stage. Analysis conducted on each of the aqueous samples consists of acid digestion, followed by atomic absorption spectroscopy. Using this method and the knowledge of selective filtration of each of the stages, (Stage 1=organically bound Hg, Stage 2=elemental Hg, Stage 3=ionic Hg), a subtraction method is employed to elucidate concentrations of each species of Hg in the stream. This was previously impossible due to the nature of non-selectivity of atomic absorption spectroscopy.

In addition, the first filtration stage is optionally removed from the filter housing after a specified time period, for total organic analysis. This is carried out by filter sectioning, hexane extraction, and running gas chromatography mass spectrometry. This is for elucidation of organic specie types and concentrations. Total organic concentration in the inlet stream is determined by knowing the complete mass of the filter, the mass of the section subjected to extraction, and the flow rate and time the filter was subjected to, thereby allowing the analyst to determine concentration in the stream per volume.

In the instance of a gaseous stream, the stream is sampled before flowing through the system with an gaseous grab sample, or a sorption tube sample. The system is run for the prescribed period of time and then taken off line and shipped to an analytical laboratory in its entirety.

Each vessel is opened and the filtration media is removed to be analyzed. In the first stage, a cross section of the filter is extracted. This cross section is prepared with acid digestion and then followed by atomic absorption spectroscopy. Stages 2 and 3 are cross-sectioned and analyzed in this fashion. The mass of the cross-sectioned portions is recorded and a mercury concentration by mass of filter is determined. Knowing the complete mass of the filter, and the flow rate and time the filter was subjected to, analyst is able to determine concentration of mercury in the gaseous stream per volume.

In addition, as in the instance of the aqueous stream, in the gaseous stream case as well, the first stage filtration media is optionally removed from the filter housing after the specified time period, for total organic analysis. This is again carried out by filter sectioning, hexane extraction, and running gas chromatography mass spectrometry. This is for elucidation of organic specie types and concentrations. Total organic concentration in the inlet stream is determined by knowing the complete mass of the filter; the mass of the section subjected to extraction, and the flow rate and time the filter was subjected to, thereby allowing the analyst to determine concentration in the stream per volume.

Once the characterization of the three types of mercury is achieved, the data can then be utilized to determine the capacity of the three different filtration stages required to reduce the mercury content in the main stream to a desired level, or can be used for other purposes.

BRIEF DESCRIPTION OF DRAWINGS

The invention is diagrammatically illustrated, by way of example, in the drawings appended hereto, in which.

DESCRIPTION OF PREFERRED EMBODIMENT

Figure 1:
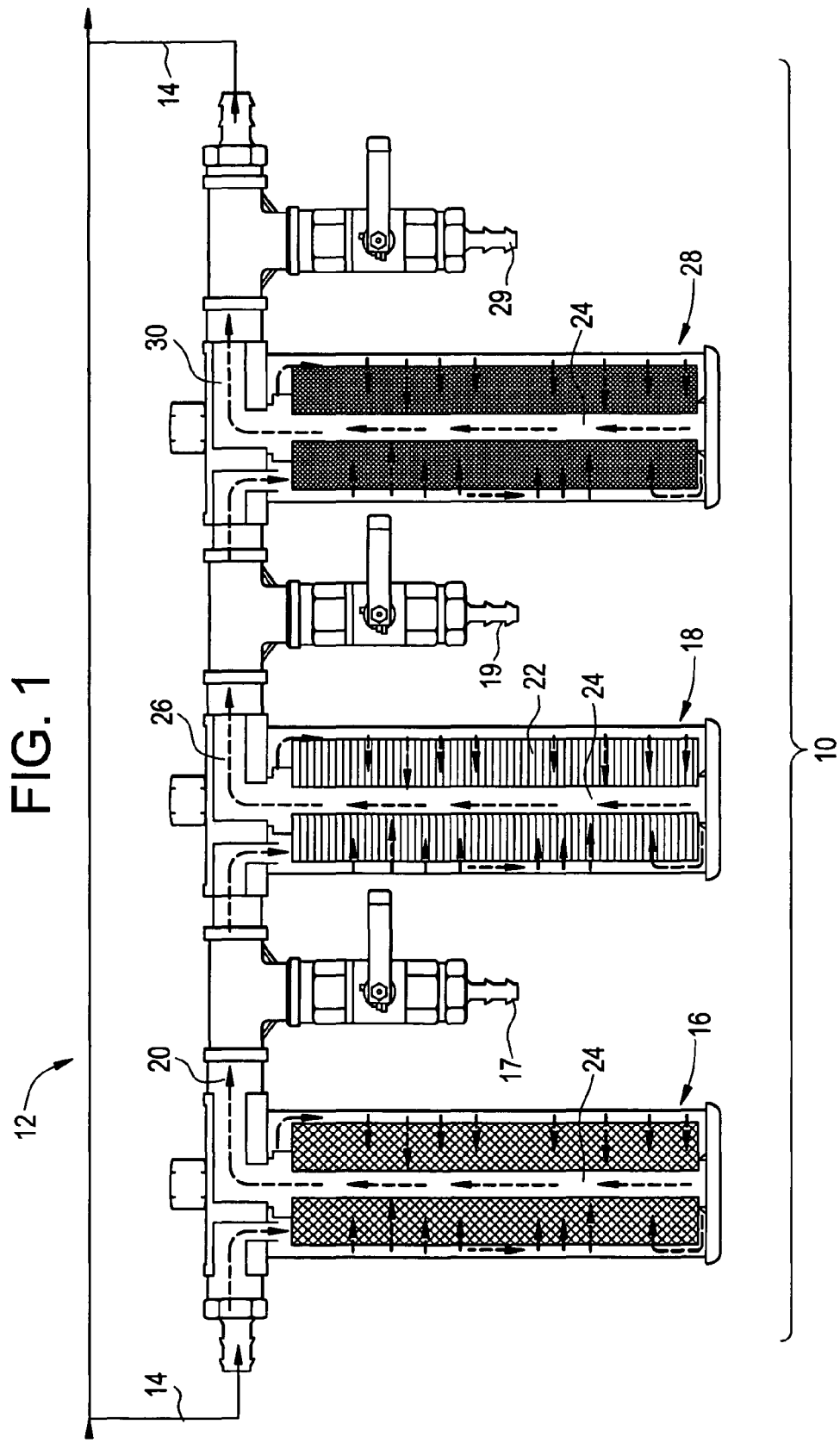
FIG. 1 is a schematic partially cross-sectioned diagram, illustrating a system operating in accordance with the present invention.

FIG. 1 is a schematic, partially cross-sectioned diagram illustrating a system 10 operating in accordance with the present invention. For purposes of concrete illustration, system 10 will be first described on the assumption that it is operating upon an aqueous stream, such as a produced water stream as discussed above. System 10 is thus supplied by a side stream 14 (e.g. 1 to 5 gal/min) diverted from the primary stream 12 (e.g. 100s to 1000s of gal/min of produced water), and allowed to operate for a selected sampling period, depending on the influent concentrations and flow. The first filtration stage 16 preferably comprises a container within which is a fluid pervious filtration media which has been infused with an oleophilic absorption composition, whereby the removed organically bound Hg contaminants are immobilized at the media.

In accordance with the invention, the influent side stream 14 at stage 16 is thus passed through absorption composition-infused filtration media (referred to for convenience herein as an "ACI filtration media"). The flow pattern through the filter stage is shown by the arrows. The ACI filtration media preferably comprises a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby the organically-bound Hg contaminants are immobilized at the media. Filtration media of this type are disclosed in detail in the present applicant's U.S. Pat. No. 6,180,010, the disclosure of which is incorporated herein by reference. The filters of the U.S. Pat. No. 6,180,010 are thus oleophilic in nature and suitable as the first filtration stage of the present invention. In that capacity they cooperate with the remaining downstream second and third mercury removal filtration stages. As set forth in that U.S. patent, the filtration media (which is infused) can comprise a non-woven polypropylene, paper, a porous ceramic, a porous metal, a mineral particulate such as vermiculite or perlite, or so forth.

The term "absorbent composition" as used herein is one of convenience for identifying the said compositions of my aforementioned patent, and will be used as well in referring to the compositions used in first filtration stage 16 of the present invention. The specific mechanism by which the noxious Hg contaminants are removed from aqueous streams by conjunctive use of such "absorbent compositions" is not completely understood, and could include attachment and/or fixation of such contaminants by mechanisms that technically involve various physical and/or chemical interactions. The term "absorbent" as used herein is intended to encompass all of these possible mechanisms.

The absorbent compositions used herein in the ACI filtration media are also disclosed and utilized in the present inventor's U.S. Pat. Nos. 6,805,727; 5,437,793; 5,698,139; 5,837,146, and 5,961,823 (all of which disclosures are hereby incorporated by reference) They have extremely strong affinities for the aforementioned organically bound mercury contaminants in the aqueous stream. Accordingly when such streams containing these contaminant particles are passed through fluid-pervious filtration media incorporating these compositions, the mentioned contaminants are immobilized at the media, as a result of which concentration levels of the mentioned organically bound mercury contaminants in the stream filtrate from filtration stage 16 may be reduced to very low values, in some instances below detectable limits.

The oleophilic first filtration stage 16, is thus used in system 10 upstream of the second filtration stage 18 in order to remove and retain particulate organically bound mercury contaminants in the aqueous stream prior to the effluent flow 20 from stage 16 being acted upon by the metal capillary ("MC") filter or filters at second filtration stage 18.

Heretofore there has been no technology that is considered optimal for capture of the mercury in its elemental form. Although coalescers, brominated adsorbents, and other methods have been used, they either lack effectiveness or have significant negative aspects such as generation of large amounts of mercury-polluted material to be landfilled. Coalescers lack effectiveness due to the extremely small size and high surface tension of the droplets and also due to the lack of affinity for mercury of typical coalescer materials. Also known is a process based on photochemical oxidation. This has chiefly been known for use in treating flue gas wherein ultraviolet (UV) light is introduced into the flue gas, to convert elemental mercury to an oxidized form (i.e. mercuric oxide, mercurous sulfate, and mercurous chloride). Once in the oxidized form, mercury can be collected in existing air pollution control devices such as wet $SO_2$ scrubbers, electrostatic precipitators, and baghouses (fabric filters).

None of the foregoing techniques, however, have been fully successful in treating aqueous or gaseous systems of the type with which the present invention is concerned. The problem associated with capturing finely dispersed elemental mercury at the second filtration stage 18 is primarily one of overcoming the surface tension of the dispersed minute mercury droplets in order to allow the liquid mercury to wet out on a surface. In accordance with the present invention, a metallic capillary surface at filtration stage 18 is contacted with the aqueous or gaseous stream, causing the mercury droplets to deposit on the capillary surface and by capillary action to coalesce with other of such droplets to form increasingly large drops of mercury.

At the second filtration stage 18, the above phenomena is exploited by employing a capillary surface-bearing substrate, preferably comprised of finely braided strands of copper wire (e.g. approximately 40-gauge, 3 mil diameter, 192 wires/strand) which has an integral surface deposition of a precious metal such as gold. Gold has a demonstrated affinity for mercury. Generally when gold is deposited on copper, an intermediate metal such as nickel is first plated on the copper to act as a barrier to prevent inter-metallic formation of the copper and gold. In the present invention, however, this intermetallic formation is desirable as it results in a highly stable substantially unitary structure in the strands of the braid, which resist deterioration from the thermal cycling imposed by typical environments in which the invention is employed.

In contrast, were a barrier layer of nickel present between the copper and gold, peeling or undercutting of the gold surface would over time become a serious problem.

The braided materials used in the filter or filters at filtration stage 18 are of a type that has been well known in the prior art as "solder wicks" because of their use to remove a solder connection. Such solder wicks are made of metal strands braided to form narrow interstices between the individual strands and to thereby provide a capillary surface at the wick's exterior. To form the wick the fine metal strands are typically braided together in the form of a tube, which is then flattened to make a braided ribbon. In a braided ribbon, the strands all extend in the longitudinal direction along the tube. The individual strands are in rather close engagement, yielding a ribbon with a limited volume between strands within which solder may be drawn. In one type of solder operation, the wick is placed on the solder connection and the connection is heated through the wick with a soldering iron. The solder melts and is drawn up onto the wick by capillary forces. Such solder wicks are generally made of copper wire.

Figures 2, 2A:
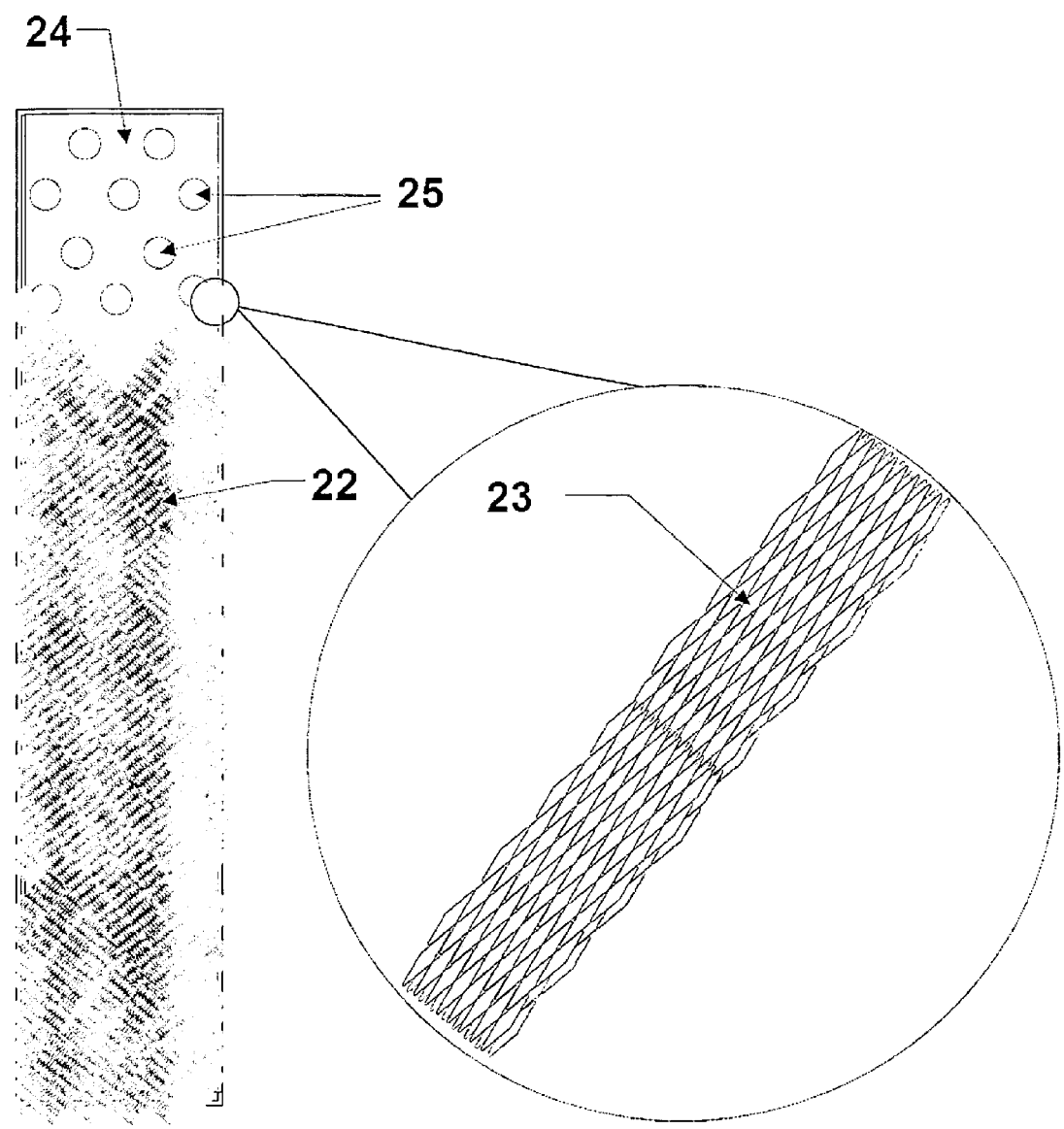
FIG. 2 is a schematic elevational view of a portion of the first filtration stage, showing the core of the filter and portions of the braid which is wound on the core.
FIG. 2A is an enlarged view of a portion of the braid in FIG. 2.

In U.S. Pat. No. 3,627,191 further details of such a solder wick are discussed, such as that the wick disclosed therein comprises a braid of strands of 40-gauge copper wire and the strands are in groups of four. The wick is braided from a machine having 16 heads so that the wick is 64 strands thick with 23 tucks 27 per inch. Other grades of wire and braiding patterns can also be used, e.g., 96 strands of 44 gauge can be braided in 16 groups of six strands, etc. Solder wicks have also been proposed for production by other than braiding. For example, U.S. Pat. No. 4,416,408 mentions the use of an open-mesh structure prepared by "weaving, stranding, braiding, knitting or crochetting", the preferred process therein involving the use of a knitting machine, which results in the aforementioned lower wire diameter limit of 0.1 mm. Regardless, the fundamental requirement is that the wick have a capillary surface capable of wicking the molten solder, and braided wicks have been found most suitable for this function. Although various open mesh structures such as discussed above are useable in the present invention if they possess an adequate capillary surface, the braided wicks are the preferred material for use in the present invention, In the second filtration stage 18 of the present invention, a preferred braided wire 22 for the filter or filters is formed of copper and is preferably gold plated. The flattened ribbon-shaped wick or ribbon 23 (FIGS. 2 and 2A) can be wrapped around a filter or a metal core in the preferred form of a tube 24, with the wire strands all extending in the longitudinal direction along the tube, and the ribbon being in one or multiple layers so as to achieve the desired degree of filtration efficiency. The metal tube 24 has porous walls, e.g. by being perforated at openings 25, and the braid, despite the contact made by the mercury droplets with the capillary surface, is relatively pervious to flow of the effluent stream 20 from first stage 16 through them so that the aqueous or gaseous stream in which the mercury droplets are dispersed can be flowed from the tube to the braid or from the braid to the tube, to enable contacting of the gold plated metallic capillary surface with the dispersed mercury droplets. Stream flow through second stage 18 is again shown by the arrows, and as shown is preferably from the outer walls of the container toward the center and then upwardly and out as effluent stream 26. Such contact causes the droplets to deposit on the capillary surface and by capillary action to coalesce with other of said droplets to form increasingly large drops of mercury. When wound in this way around a core, high removal efficiency of the elemental mercury is achieved at very low differential pressures as the aqueous stream passes through the wound core. The braided structure of the substrate results in interstitial areas of extreme contact angle (less than 45 degrees), which is able to entrap the droplets. The combination of this contact angle, along with the affinity of gold for mercury results in the de-dispersion of the droplets and wetting out on the substrate.

The detailed structure and mode of operation of second filtration stage 18 substantially corresponds to the device depicted and described in the present inventor's copending application Ser. No. 12/459,389, filed Jun. 30, 2009, of which the present application is a U.S. continuation-in-part. In that application, the quantities of mercury collected are comparatively large, whereby the large drops formed at the capillary surface tend to flow downwardly, i.e. the surface may be oriented to allow the mercury drops to flow by gravitational forces and capillary action to the lowermost portions of the surface or an extension of same, where they accumulate. The accumulated mercury can be collected at a suitable vessel or the like. In the present invention, however, all of the capillaries have to be saturated before any excess drips to the bottom of the vessel. The limited duration of the evaluation period is usually not sufficient to accumulate that much Hg. Each gram of braid will take at least 0.1 gm of Hg before enough Hg for drippage has accumulated. Considering that influent concentrations are in the tens to hundreds of ppb range the intercepted Hg will still be in the braid. In case the Hg concentrations are very high and there is accumulated Hg in the bottom of the vessel, this will be measured and taken into account and added to how much is trapped by the braid.

In the present invention, the preferred braided wire 22 is of copper and gold plated and the flattened ribbon-shaped wick 23 is wrapped around a filter or the porous wall metal tube 24 in one or multiple layers so as to achieve the desired degree of filtration efficiency. When wound in this way, high removal efficiency of aerosol mercury is achieved at very low differential pressures. For example, in the case where a gaseous flow is being evaluated, for a three layer thickness of braid around a steel tube with wall perforations as in FIGS. 2 and 2A, differential pressure is typically only between 1 to 3 PSI at a gas stream flow rate of 600 million ft$^3$ per day.

The effluent stream 26 from which the elemental mercury has been removed exits the second filtration stage stage and proceeds to the third filtration stage 28. At the third filtration stage 28 of the present invention, the effluent stream 26 from the second stage 18 is passed through a filter or filters, where it is subjected to conditions, which remove the ionic mercury. In the case of an aqueous stream, this can be readily accomplished by passing the stream though a granular media impregnated with one or more chemical agents that are able to effect the desired precipitation. The granular media can be composed of carbon, clay, paper, mineral particulates such as perlite, etc., and the precipitating agents can include, but are not limited to, calcium sulfate, sulfides and thiols. These substrates may be packed or otherwise disposed in a cartridge or canister filter; or can be formed into bag filters which can be emplaced in canisters through which the contaminated water is flowed. The effluent stream 30 from third filtration stage 28 is then returned to the main or primary aqueous stream 12.

In the instance of a gaseous stream, the third stage is removed after the period of operation, and the collecting media (typically activated carbon) is subjected to chromatographic and/or spectrometric analysis. Inorganic salts of Hg with Cl, S or oxygen will behave as acids upon exposure to alkaline media such as the modified carbon resulting in formation of elemental Hg which will then be adsorbed onto the carbon substrate. In this context "ionic mercury" essentially means or is synonymous with inorganic mercury salts. Such salts may be present in the gaseous steam where they are hydrated by water vapor in the gases. Reaction products at the third filter stage 28 media will predominately be calcium chloride, sulfide, oxide or hydroxide and elemental Hg which will be adsorbed on the carbon media.

For an aqueous stream, the system 10 is typically supplied by a side stream 14 having a flow of e.g. 1 to 5 gal/min from the primary or main stream 12 the flow of which can e.g. be of 100s to 1000s of gal/min, and allowed to operate for a sampling period that depends on the influent concentrations. Each one of the three stages accumulates the species of mercury for which it has particular affinity. By concentrating the different species over a period of time, this approach overcomes the difficulties caused by attempting to spot sample for low concentrations, fluctuation in influent concentration, and alteration of species after sampling.

In the case of an aqueous stream, the stream is sampled before flowing through the first filtration stage with an aqueous grab sample. Filtered aqueous samples are taken after each stage. Analysis conducted on each of the aqueous samples consists of acid digestion, followed by atomic absorption spectroscopy. Using this method and the knowledge of selective filtration of each of the stages, (Stage 1=organically bound Hg, Stage 2=elemental Hg, Stage 3=ionic Hg), a subtraction method is employed to elucidate concentrations of each species of Hg in the stream. This was previously impossible due to the nature of non-selectivity of atomic absorption spectroscopy.

In addition, the first filtration stage is optionally removed from the filter housing after a specified time period, for total organic analysis. This is carried out by filter sectioning, hexane extraction, and running gas chromatography mass spectrometry. This is for elucidation of organic specie types and concentrations. Total Organic Concentration in the inlet stream is determined by knowing the complete mass of the filter, the mass of the section subjected to extraction, and the flow rate and time the filter was subjected to, hereby allowing the analyst to determine concentration in the stream per volume.

After the sampling period, each of the stages is removed and analyzed for Hg. At this stage, testing can be destructive because characterization of the species was done during sampling. Each one of the stages can be analyzed by acid digestion followed by atomic absorption spectrophotometry (AA) or induction-coupled plasma (ICP) or a number of other well-known spectrographic techniques.

In the instance of a gaseous stream the system 10 may be connected through a regulator at 1 to 80 pounds per square inch (psi). The system is typically engaged from 1 to 8 hours. At the end of the sampling period the system is disengaged and the three filtration stages are analyzed for content of the particular mercury species collected at the stage.

Once such an analysis is in hand, the data presents an accurate picture of the relative proportions of the three species of mercury present in the primary aqueous stream of interest, as well as the concentrations of the species. This analysis may then be dependably used to design a system for removing the mercury contamination from the primary stream. Thus e.g. the analysis can be used to establish that a specific number of filtration units corresponding to stage one of the present invention are required, a specified number of filtration units as in stage two, and a specific number of filtration units as in stage three.

While the present invention has been set forth in terms of specific embodiments thereof, the instant disclosure is such that numerous variations upon the invention are now enabled to those skilled in the art, which variations yet reside within the scope of the present teaching. Accordingly, the invention is to be broadly construed and limited only by the scope and spirit of the present disclosure.

The invention claimed is:

1. A method for facilitating removal of mercury from a primary fluid stream of interest which is contaminated with organically-bound, elemental, and ionic mercury species, comprising:
   (1) analyzing the said stream to characterize the relative content of the said organically-bound, elemental, and ionic mercury species present therein by the steps of (a) forming a diverted side stream from the primary stream, and (b) passing the side stream successively through three in series filter stages, the first of said stages being effective to capture said organically bound mercury, the second of said stages being effective to capture said elemental mercury, and the third of said stages being effective to capture said ionic mercury;
   (2) continuing the said side stream flow through the said filter stages for a predetermined period;
   (3) upon conclusion of the said period determining the quantity of mercury collected at each of the said filtration stages; and
   (4) utilizing the data resulting from step (3) to determine the capacity of the three different said filtration stages required to reduce the mercury content in said main stream to a desired level.

2. The method of claim 1, wherein the said primary stream is gaseous.

3. A method in accordance with claim 1, wherein the quantity of mercury collected at a said filtration stage is determined by destructive testing of the filtration media at said stage at the end of the said predetermined period.

4. The method of claim 1, wherein the said primary stream is aqueous.

5. The method of claim 4, wherein the said predetermined period is in the range of from one day to multiple weeks.

6. The method of claim 4, wherein the said primary stream comprises a produced water stream.

7. A method in accordance with claim 4, wherein the quantity of mercury collected at a said filtration stage is determined by evaluating the difference between the concentration of mercury at the input stream to the stage at the beginning of the predetermined period, and the concentration of mercury at the output flow from the said stage at the end of the said predetermined period.

8. The method of claim 1, wherein said first filtration stage captures the organically bound mercury by contacting the side stream with a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby the removed contaminants are immobilized at the media.

9. The method of claim 8, wherein said second filtration stage captures the elemental mercury by contacting the side stream with a metallic capillary surface causing said elemental mercury to deposit as droplets on said surface and by capillary action to coalesce with other of said droplets to increasingly wet the said surface.

10. The method of claim 9, wherein said third filtration stage collects the ionic mercury by contacting the side stream with a media that reacts with the ionic mercury.

11. The method of claim 10, wherein the said stream is aqueous, and wherein said third filtration stage collects the ionic mercury by contacting the side stream with a media impregnated with chemical agents that are able to precipitate the ionic mercury.

12. The method of claim 10, wherein the said stream is gaseous, and wherein said third filtration stage collects the ionic mercury by contacting the said side stream with granules of activated carbon.

13. A method in accordance with claim 9, wherein the capillary surface is defined at the surface of a wick made of metal strands braided to form narrow interstices between the individual strands which thereby provide said capillary surface at the wick's exterior.

14. A method in accordance with claim 13, wherein the metallic capillary surface is gold plated.

15. A method in accordance with claim 14, wherein the capillary surface is defined at the surface of a wick made of metal strands braided to form narrow interstices between the individual strands which thereby provide said capillary surface at the wick's exterior.

16. A method in accordance with claim 15, wherein said metal strands comprise copper.

17. A method in accordance with claim 16, wherein said braided strands are flattened into a ribbon which is wound on a core with the said strands all extending in the longitudinal direction along the core, the capillary surface being defined at the surface of said wound ribbon.

18. A method for analyzing a primary fluid stream of interest which is contaminated with organically-bound, elemental, and ionic mercury species, in order to quantify the concentrations in said stream of said species, comprising:
   (1) analyzing the said stream to characterize the relative content of the said organically-bound, elemental, and ionic mercury species present therein by the steps of (a) forming a diverted side stream from the primary stream, and (b) passing the side stream successively through three in series filter stages, the first of said stages being effective to capture said organically bound mercury, the second of said stages being effective to capture said elemental mercury, and the third of said stages being effective to capture said ionic mercury;
   (2) continuing the said side stream flow through the said filter stages for a predetermined period; and
   (3) upon conclusion of the said period determining the quantity of mercury collected at each of the said filtration stages.

19. The method of claim 18, wherein the said primary stream is gaseous.

20. The method of claim 18, wherein the said primary stream is aqueous.

21. The method of claim 20, wherein the said predetermined period is in the range of from one day to multiple weeks.

22. The method of claim 20, wherein the said primary stream comprises a produced water stream.

23. The method of claim 18, wherein said first filtration stage captures the organically bound mercury by contacting the side stream with a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby the removed contaminants are immobilized at the media.

24. The method of claim 23, wherein said second filtration stage captures the elemental mercury by contacting the side stream with a metallic capillary surface causing said elemental mercury to deposit as droplets on said surface and by capillary action to coalesce with other of said droplets to increasingly wet the said surface.

25. The method of claim 24, wherein said third filtration stage collects the ionic mercury by contacting the side stream with a media that reacts with the ionic mercury.

26. The method of claim 25, wherein the said stream is aqueous, and wherein said third filtration stage collects the ionic mercury by contacting the side stream with a media impregnated with chemical agents that are able to precipitate the ionic mercury.

27. The method of claim 25, wherein the said stream is gaseous, and wherein said third filtration stage collects the ionic mercury by contacting the said side stream with granules of activated carbon.

28. A method in accordance with claim 25, wherein the capillary surface is defined at the surface of a wick made of metal strands braided to form narrow interstices between the individual strands which thereby provide said capillary surface at the wick's exterior.

* * * * *